United States Patent

Chen

(10) Patent No.: US 10,193,154 B2
(45) Date of Patent: Jan. 29, 2019

(54) CATHODE COMPOSITION FOR PRIMARY BATTERY

(71) Applicant: Medtronic, Inc., Minneapolis, MN (US)

(72) Inventor: Kaimin Chen, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 438 days.

(21) Appl. No.: 13/755,994

(22) Filed: Jan. 31, 2013

(65) Prior Publication Data

US 2014/0212736 A1    Jul. 31, 2014

(51) Int. Cl.
| | |
|---|---|
| H01M 4/54 | (2006.01) |
| H01M 4/06 | (2006.01) |
| H01M 4/62 | (2006.01) |
| H01M 6/16 | (2006.01) |
| A61N 1/378 | (2006.01) |
| H01M 4/36 | (2006.01) |
| H01M 4/58 | (2010.01) |
| A61N 1/375 | (2006.01) |

(52) U.S. Cl.
CPC ............. *H01M 4/54* (2013.01); *A61N 1/378* (2013.01); *H01M 4/06* (2013.01); *H01M 4/628* (2013.01); *H01M 6/16* (2013.01); *A61N 1/375* (2013.01); *H01M 4/364* (2013.01); *H01M 4/58* (2013.01)

(58) Field of Classification Search
None
See application file for complete search history.

(56) References Cited

U.S. PATENT DOCUMENTS

| 3,939,006 A | 2/1976 | Kozawa |
| 4,048,387 A | 9/1977 | Lahme et al. |
| 4,391,729 A | 7/1983 | Liang et al. |

(Continued)

FOREIGN PATENT DOCUMENTS

EP         2062613 A2 *   5/2009

OTHER PUBLICATIONS

Goldstein, "Chemical kinetics of copper oxide reduction with carbon monoxide", 2011 [Available online Oct. 18, 2010], Proceedings of the Combustion Institute, vol. 33, Issue 2, pp. 2803-2810.*

(Continued)

*Primary Examiner* — Sarah A. Slifka
*Assistant Examiner* — Haroon S. Sheikh (57) ABSTRACT

In some examples, a primary battery comprising a cathode comprising at least one active material and at least one of a metal oxide and metal fluoride, wherein the active material exhibits a first discharge capacity and the at least one of metal oxide and metal fluoride exhibits a second discharge capacity at a voltage lower than the first discharge capacity; an anode comprising a metal as an electron source; and an electrolyte between the cathode and anode. The metal reacts with the electrolyte below a third discharge capacity at a voltage lower than the second discharge capacity to form a gas, where the metal reacts with the active material at the first discharge capacity, and, following the consumption of the active material of the cathode, the metal reacts with the at least one of metal oxide and metal fluoride of the cathode prior to reacting with the electrolyte below the third discharge capacity.

27 Claims, 6 Drawing Sheets

I—first discharge capacity; II—second discharge capacity; III – third discharge capacity (56) References Cited

U.S. PATENT DOCUMENTS

| | | | |
|---|---|---|---|
| 4,925,748 A | 5/1990 | Ikoma et al. | |
| 5,180,642 A * | 1/1993 | Weiss | H01M 4/36 |
| | | | 429/231.5 |
| 5,496,656 A | 3/1996 | Inamasu et al. | |
| 5,595,949 A | 1/1997 | Goldstein et al. | |
| 5,667,916 A * | 9/1997 | Ebel | H01M 4/36 |
| | | | 429/219 |
| 5,716,728 A * | 2/1998 | Smesko | H01M 6/04 |
| | | | 29/623.1 |
| 6,048,638 A | 4/2000 | Pendalwar | |
| 6,551,747 B1 * | 4/2003 | Gan | 429/245 |
| 6,872,490 B2 | 3/2005 | Leising et al. | |
| 7,629,075 B2 | 12/2009 | Miles | |
| 2004/0029005 A1 | 2/2004 | Leising et al. | |
| 2007/0072075 A1 * | 3/2007 | Gan | H01M 4/06 |
| | | | 429/209 |
| 2007/0178381 A1 * | 8/2007 | Howard | H01M 4/485 |
| | | | 429/231.7 |
| 2008/0070104 A1 | 3/2008 | Lin et al. | |

OTHER PUBLICATIONS

Gomadam et al., "Modeling Li/CF x-SVO Hybrid-Cathode Batteries," Journal of the Electrochemical Society 154(11): A1058-A1064, 2007.

* cited by examiner

CATHODE COMPOSITION FOR PRIMARY BATTERY

TECHNICAL FIELD

The disclosure relates to batteries and, more particularly, to batteries of medical devices.

BACKGROUND

Medical devices such as implantable medical devices (IMDs) include a variety of devices that deliver therapy (such as electrical simulation or drug delivery) to a patient, monitor a physiological parameter of a patient, or both. IMDs typically include a number of functional components encased in a housing. The housing is implanted in a body of the patient. For example, the housing may be implanted in a pocket created in a torso of a patient. The housing may include various internal components such as batteries and capacitors to deliver energy for therapy delivered to a patient and/or monitoring a physiological parameter of a patient.

SUMMARY

In some aspects, the disclosure is directed to a primary battery, such as a lithium primary battery, for use, e.g., in a medical device, and techniques for manufacturing the battery. The primary battery may include an anode including a metal as an electron source, a cathode including an active material, and an organic electrolyte enclosed within a battery housing. The cathode also includes a metal oxide and/or metal fluoride selected such that, when the active material of the cathode is substantially consumed by the reaction with the metal of the anode, the metal of the anode reacts with the metal oxide and/or metal fluoride rather than the organic electrolyte. In this manner, the amount of gas produced within the housing as a result of the reaction of the anode metal with the organic electrolyte may be reduced or substantially eliminated depending on the amount of metal oxide and/or metal fluoride in the cathode compared to the excess metal in the anode.

In one example, the disclosure is directed to a primary battery comprising a cathode comprising at least one active material and at least one of a metal oxide and metal fluoride, wherein the active material exhibits a first discharge capacity and the at least one of metal oxide and metal fluoride exhibits a second discharge capacity at a voltage lower than the first discharge capacity; an anode comprising a metal as an electron source; and an electrolyte between the cathode and anode, wherein the metal reacts with the electrolyte below a third discharge capacity at a voltage lower than the second discharge capacity to form a gas, and wherein the metal reacts with the active material at the first discharge capacity, and, following the consumption of the active material of the cathode, the metal reacts with the at least one of metal oxide and metal fluoride of the cathode prior to reacting with the electrolyte below the third discharge capacity.

In another example, the disclosure is directed to an implantable medical device comprising a housing and a primary battery within the housing. The primary battery comprises a cathode comprising at least one active material and at least one of a metal oxide and metal fluoride, wherein the active material exhibits a first discharge capacity and the at least one of metal oxide and metal fluoride exhibits a second discharge capacity at a voltage lower than the first discharge capacity, an anode comprising a metal as an electron source, and an electrolyte between the cathode and anode. The metal reacts with the electrolyte below a third discharge capacity at a voltage lower than the second discharge capacity to form a gas, and wherein the metal reacts with the active material at the first discharge capacity, and, following the consumption of the active material of the cathode, the metal reacts with the at least one of metal oxide and metal fluoride of the cathode prior to reacting with the electrolyte below the third discharge capacity.

The details of one or more examples of the disclosure are set forth in the accompanying drawings and the description below. Other features, objects, and advantages of the disclosure will be apparent from the description and drawings, and from the claims.

DETAILED DESCRIPTION

A variety of medical devices may utilize primary batteries. For example, an implantable medical device (IMD) that provides cardiac rhythm management therapy to a patient may include a primary battery to supply power for the generation of electrical stimulation. For ease of illustration, examples of the present disclosure will be described primarily with regard to lithium primary batteries. However, as will be apparent from the description herein, examples of the disclosure may include primary batteries that are not lithium primary batteries, e.g., primary batteries that utilize a metal as an electron source for the anode. Accordingly, instances in which lithium is described are also applicable to other metal electron sources besides that of lithium.

In some examples, a lithium primary battery may include a lithium anode and a hybrid cathode formulation, such as, e.g., carbon monofluoride ($CF_x$) and silver vanadium oxide (SVO) hybrid, with an organic electrolyte all enclosed within a battery housing. In such cases, it may be difficult to balance the amount of lithium versus cathode composition such that that the battery is lithium-limited. For primary batteries that include excess lithium in the anode, following the discharge of the cathode composition throughout the service life of the battery, the lithium may react with the organic electrolyte which may cause the formation of gas in the battery housing. In such cases, particularly those cases in which an implanted medical device may not be removed from a patient immediately following the consumption of the active material of the cathode, the primary battery may be designed to account for the resulting formation of gas within the housing following the consumption of the active material of the cathode. For example, the size of the housing may be increased to account for the increase in pressure due to the formation of the gas and allow for the battery housing to maintain sufficient structural integrity. However, the resulting increase in size of the lithium primary battery may be undesirable, e.g., as increasing the size of a lithium primary battery may cause an increase the overall size of the implantable medical device enclosing the lithium primary battery for operational power and reducing the packing density of the device.

In accordance with one or more examples of the disclosure, a lithium primary battery (or other primary battery) may include a lithium-containing anode (or other metal) as an electron source, a cathode including an active material, and an organic electrolyte enclosed within a battery housing. In addition, the cathode also includes metal oxide and/or metal fluoride selected such that, when the active material of the cathode is substantially consumed by the reaction with the lithium (or other metal) of the anode, the lithium (or other metal) reacts with the metal oxide and/or metal fluoride rather than the organic electrolyte. For example, the metal oxide or metal fluoride material incorporated into the cathode composition may exhibit a discharge capacity at a voltage versus lithium that is less than that of the active material of the cathode but greater than the discharge voltage at which the lithium reacts with the organic electrolyte. Example metal oxides and fluorides may include cupric oxide (CuO), cuprous oxide ($Cu_2O$), vanadium oxide ($V_2O_4$), chromium oxide ($Cr_2O_3$), vanadium fluoride ($VF_3$), Iron fluoride ($FeF_2$), bismuth fluoride ($BiF_3$) and manganese fluoride ($MnF_2$).

The reaction of the metal oxide or metal fluoride may consume at least a portion of the excess lithium of the anode following the consumption of the active material of the cathode. In this manner, depending on the amount of metal oxide or metal fluoride in the cathode compared to the excess lithium in the anode, the amount of gas produced within the housing as a result of the reaction of the lithium with the organic electrolyte may be reduced or substantially eliminated within the battery housing. In some examples, the use of such a lithium primary battery may allow for a decrease in overall size of a medical device and increase in packing density compared to that of a medical device incorporating a lithium primary battery without such a metal oxide or metal fluoride in the cathode composition.

Figure 6:
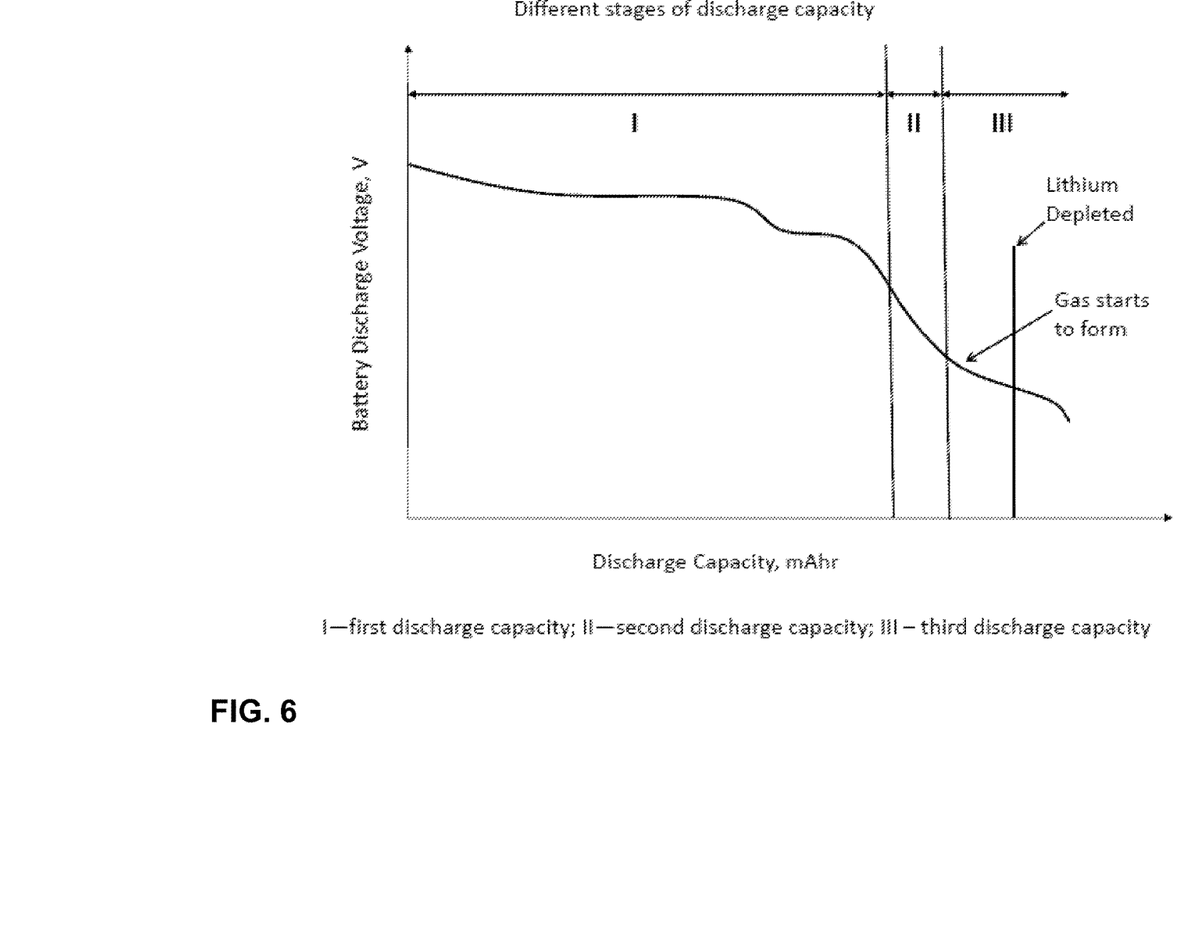
FIGS. 6-8 are representative plots illustrating discharge voltage versus discharge capacity for three example primary batteries.
Figure 7:
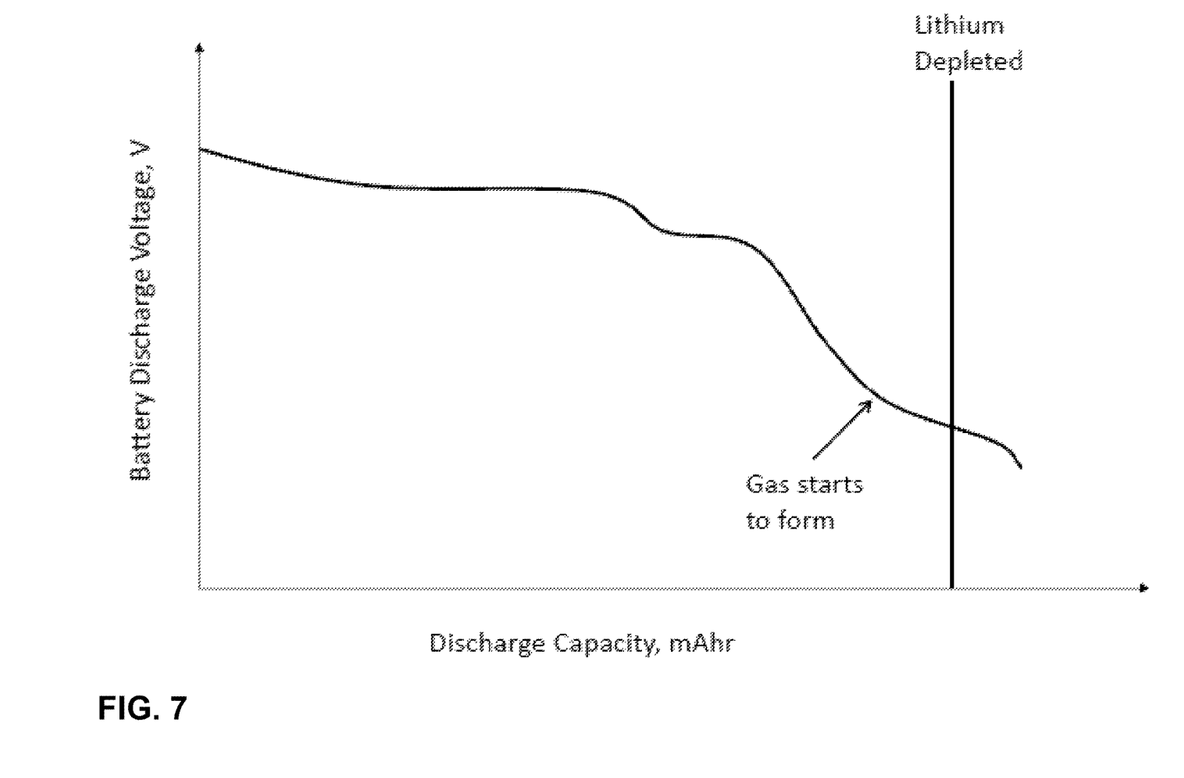
Figure 8:
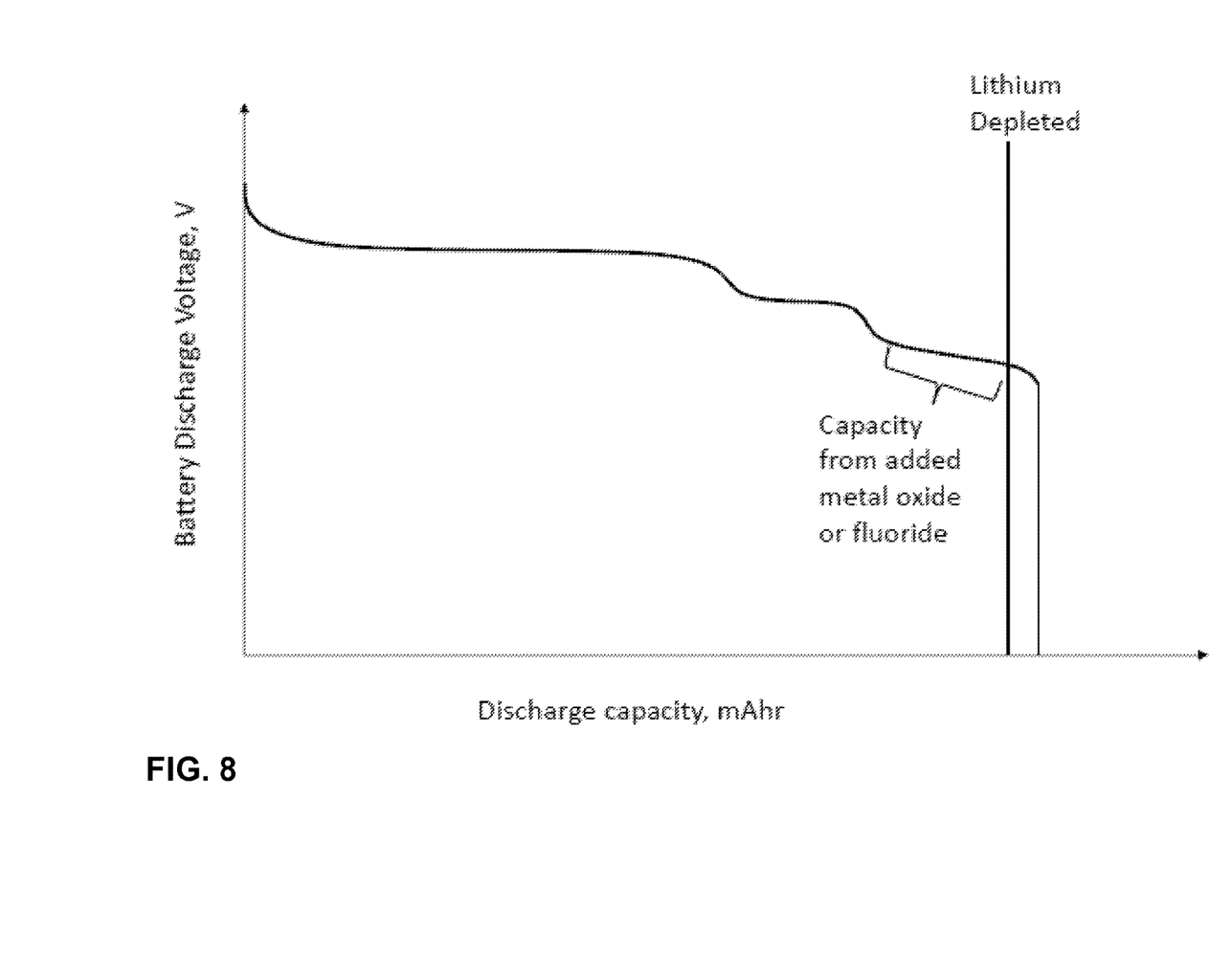

FIGS. 6-8 are representative plots illustrating discharge voltage versus discharge capacity for three example primary batteries. FIG. 6 illustrates an example primary battery having three stages. Stage I generally corresponds to the discharge capacity during the operational life of a battery, e.g., according to the battery discharge voltage during Stage I. Stage II follows Stage I and corresponds to the remaining un-usable capacity of the active materials above the gas formation voltage. Following Stage II, with substantially no active material to react with the lithium (or other metallic electron source) of the anode, the voltage of the battery reaches a voltage at which the lithium reacts with the electrolyte. This reaction forms gas within the battery housing and continues until the lithium in the anode is depleted.

FIG. 7 is a plot similar to that of FIG. 6 which illustrates discharge capacity versus discharge voltage for an example battery in which gas forms from the reaction of lithium with electrolyte following the consumption of active matter of the cathode. Again, the gas formation continues until the lithium in the anode of depleted.

FIG. 8 is a plot illustrating the discharge capacity versus discharge voltage for an example battery in accordance with one or more examples of the disclosure. As shown, unlike that of FIG. 7, following the consumption of the active material in the cathode, that cathode includes a metal oxide and/or metal fluoride with a discharge capacity at a voltage less than that of the active material but greater than that at which the lithium reacts with the electrolyte to form a gas. The additional discharge capacity of the metal oxide and/or metal fluoride in the cathode allows for the reaction of the lithium with the metal oxide and/or metal fluoride, and may consume substantially all (as in the case of FIG. 8) or at least some of the excess lithium in the anode prior to the reaction of excess lithium with the electrolyte.

Figure 1:
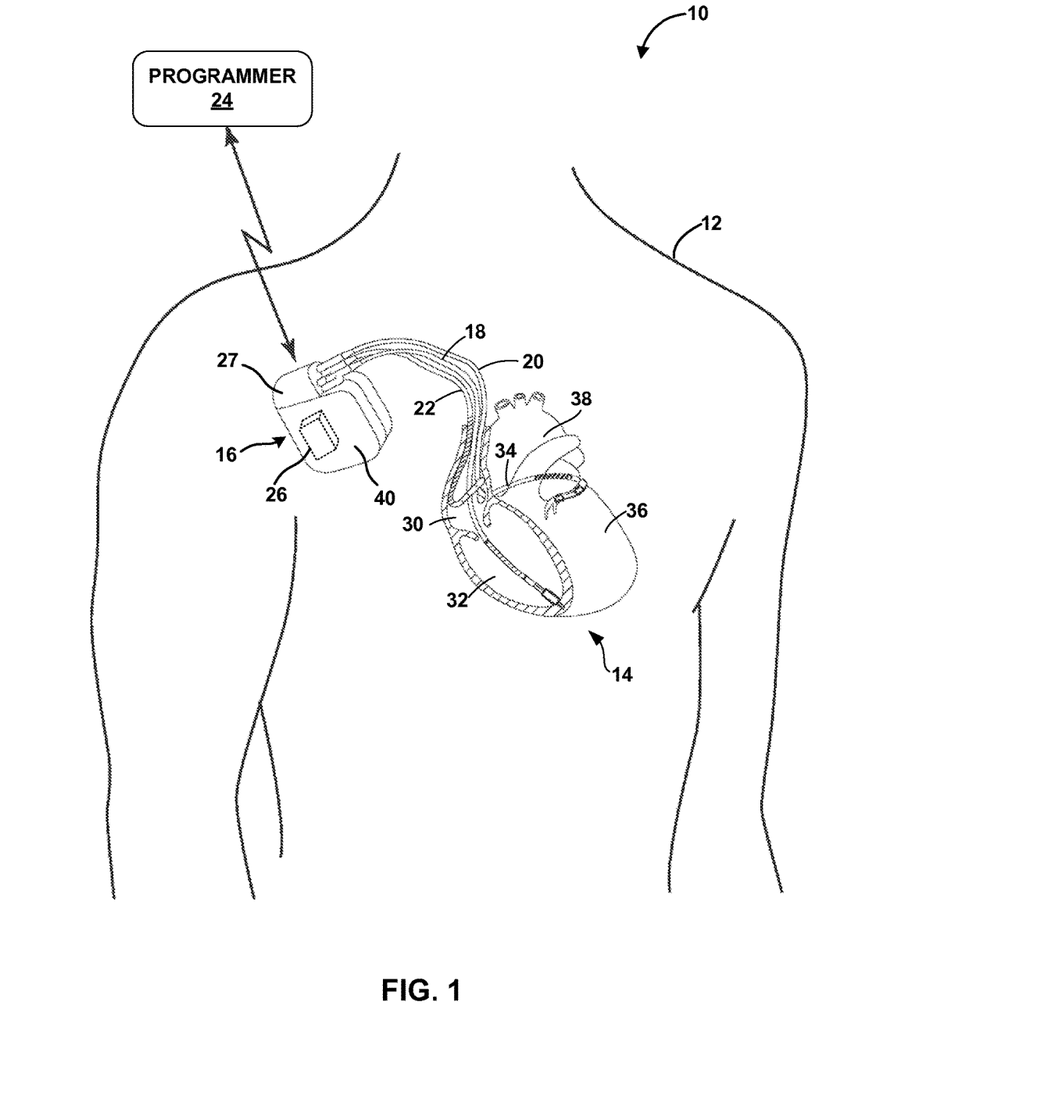
FIG. 1 is a conceptual diagram that illustrates an example therapy system that may be used to deliver therapy to a patient.

FIG. 1 is a conceptual diagram that illustrates an example therapy system 10 that may be used to provide therapy to a patient 12. Patient 12 ordinarily, but not necessarily, will be a human. Therapy system 10 may include an IMD 16, and a programmer 24. In the example illustrated in FIG. 1, IMD 16 has lithium primary battery 26 positioned within a housing 40 of the IMD 16.

While the examples in the disclosure are primarily described with regard to battery 26 positioned within housing 40 of IMD 16 for delivery of electrical stimulation to heart of patient 12, in other examples, battery 26 may be utilized with other implantable medical devices. For example, battery 26 may be utilized with an implantable drug delivery device, an implantable monitoring device that monitors one or more physiological parameter of patient 12, an implantable neurostimulator (e.g., a spinal cord stimulator, a deep brain stimulator, a pelvic floor stimulator, a peripheral nerve stimulator, or the like), a cardiac or neurological lead, or the like. In general, battery 26 may be attached to or implanted proximate to any medical device configured to be implanted in a body of a patient 12.

Moreover, while examples of the disclosure are primarily described with regard to implantable medical devices, examples are not limited as such. Rather, some examples of the batteries described herein may be employed in any medical device including non-implantable medical devices. For example, an example battery may be employed to supply power to a medical device configured delivery therapy to a patient externally or via a transcutaneoulsy implanted lead or drug delivery catheter.

In the example depicted in FIG. 1, IMD 16 is connected (or "coupled") to leads 18, 20, and 22. IMD 16 may be, for example, a device that provides cardiac rhythm management therapy to heart 14, and may include, for example, an implantable pacemaker, cardioverter, and/or defibrillator that provides therapy to heart 14 of patient 12 via electrodes coupled to one or more of leads 18, 20, and 22. In some examples, IMD 16 may deliver pacing pulses, but not cardioversion or defibrillation shocks, while in other examples, IMD 16 may deliver cardioversion or defibrillation shocks, but not pacing pulses. In addition, in further examples, IMD 16 may deliver pacing pulses, cardioversion shocks, and defibrillation shocks.

IMD 16 may include electronics and other internal components necessary or desirable for executing the functions associated with the device. In one example, IMD 16 includes one or more processors, memory, a signal generator, sensing module and telemetry modules, and a power source. In general, memory of IMD 16 may include computer-readable instructions that, when executed by a processor of the IMD, cause it to perform various functions attributed to the device herein. For example, a processor of IMD 16 may control the signal generator and sensing module according to instructions and/or data stored on memory to deliver therapy to patient 12 and perform other functions related to treating condition(s) of the patient with IMD 16.

The signal generator of IMD 16 may generate electrical stimulation that is delivered to patient 12 via electrode(s) on one or more of leads 18, 20, and 22, in order to provide (e.g., cardiac sensing, pacing signals, or cardioversion/defibrillation shocks). The sensing module of IMD 16 may monitor electrical signals from electrode(s) on leads 18, 20, and 22 of IMD 16 in order to monitor electrical activity of heart 14. In one example, the sensing module may include a switch module to select which of the available electrodes on leads 18, 20, and 22 of IMD 16 are used to sense the heart activity. Additionally, the sensing module of IMD 16 may include multiple detection channels, each of which includes an amplifier, as well as an analog-to-digital converter for digitizing the signal received from a sensing channel (e.g., electrogram signal processing by a processor of the IMD).

A telemetry module of IMD 16 may include any suitable hardware, firmware, software or any combination thereof for communicating with another device, such as programmer 24 (FIG. 1). Under the control of a processor of IMD 16, the telemetry module may receive downlink telemetry from and send uplink telemetry to programmer 24 with the aid of an antenna, which may be internal and/or external.

The various components of IMD 16 may be coupled to a power source such as battery 26, which may be a lithium primary battery. Battery 26 may be capable of holding a charge for several years. In general, battery 26 may supply power to one or more electrical components of IMD 16, such as, e.g., the signal or pulse generator, to allow IMD 16 to deliver therapy to patient 12, e.g., in the form of monitoring one or more patient parameters, delivery of electrical stimulation or delivery on a therapeutic drug fluid. Battery 26 may include a lithium-containing anode and cathode including an active material that electrochemically reacts with the lithium within an electrolyte to generate power. However, in a cathode limited battery, the operational life of battery 26 may end when substantially of the active material is consumed by the reaction with lithium. Any excess lithium may react with the electrolyte to form a gas within the housing of battery following the consumption of the active material of the cathode.

In accordance with one or more examples of the disclosure, to reduce or substantially eliminate the formation of gas due to the reaction of excess lithium with the electrolyte following the consumption of the active cathode material, the cathode of battery 26 may include a metal oxide or metal fluoride selected such that the lithium reacts with the metal oxide or fluoride of the cathode after the active material of the cathode is substantially consumed by the reaction with lithium but prior to the reaction of the lithium with the electrolyte. For example, a metal oxide and/or metal fluoride may be selected that exhibits a discharge capacity at a voltage that is lower than that of the active material in the cathode but is greater than that of the discharge voltage of the electrolyte in the battery. Depending on the amount of excess lithium of the anode and metal oxide and/or metal fluoride of cathode, the reaction of the metal oxide and/or metal fluoride and lithium may reduce or substantially eliminate that formation of gas in the housing of the battery due to reaction of the lithium and electrolyte by consuming at least some or substantially all of the excess lithium following the consumption of the active material of the cathode.

Leads 18, 20, 22 that are coupled to IMD 16 may extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. In other examples, IMD 16 may deliver stimulation therapy to heart 14 by delivering stimulation to an extravascular tissue site in addition to or instead of delivering stimulation via electrodes of intravascular leads 18, 20, 22. In the illustrated example, there are no electrodes located in left atrium 36. However, other examples may include electrodes in left atrium 36.

IMD 16 may sense electrical signals attendant to the depolarization and repolarization of heart 14 (e.g., cardiac signals) via electrodes (not shown in FIG. 1) coupled to at least one of the leads 18, 20, and 22. In some examples, IMD 16 provides pacing pulses to heart 14 based on the cardiac signals sensed within heart 14. The configurations of electrodes used by IMD 16 for sensing and pacing may be unipolar or bipolar. IMD 16 may also deliver defibrillation therapy and/or cardioversion therapy via electrodes located on at least one of the leads 18, 20, and 22. IMD 16 may detect arrhythmia of heart 14, such as fibrillation of ventricles 32 and 36, and deliver defibrillation therapy to heart 14 in the form of electrical shocks. In some examples, IMD 16 may be programmed to deliver a progression of therapies (e.g., shocks with increasing energy levels), until a fibrillation of heart 14 is stopped. IMD 16 may detect fibrillation by employing one or more fibrillation detection techniques known in the art. For example, IMD 16 may identify cardiac parameters of the cardiac signal (e.g., R-waves, and detect fibrillation based on the identified cardiac parameters).

In some examples, programmer 24 may be a handheld computing device or a computer workstation. Programmer 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16 (e.g., select values for operational parameters of IMD 16).

Programmer 24 may communicate with IMD 16 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In the example depicted in FIG. 1, IMD 16 is connected (or "coupled") to leads 18, 20, and 22. In the example, leads 18, 20, and 22 are connected to IMD 16 using the connector block 27. For example, leads 18, 20, and 22 are connected to IMD 16 using the lead connector ports in connector block 27. Once connected, leads 18, 20, and 22 are in electrical contact with the internal circuitry of IMD 16. Battery 26 may be positioned within the housing 40 of IMD 16. Housing 40 may be hermetically sealed and biologically inert. In some examples, housing 40 may be formed from a conductive material. For example, housing 40 may be formed from a material including, but not limited to, titanium, stainless steel, among others.

Figure 2:
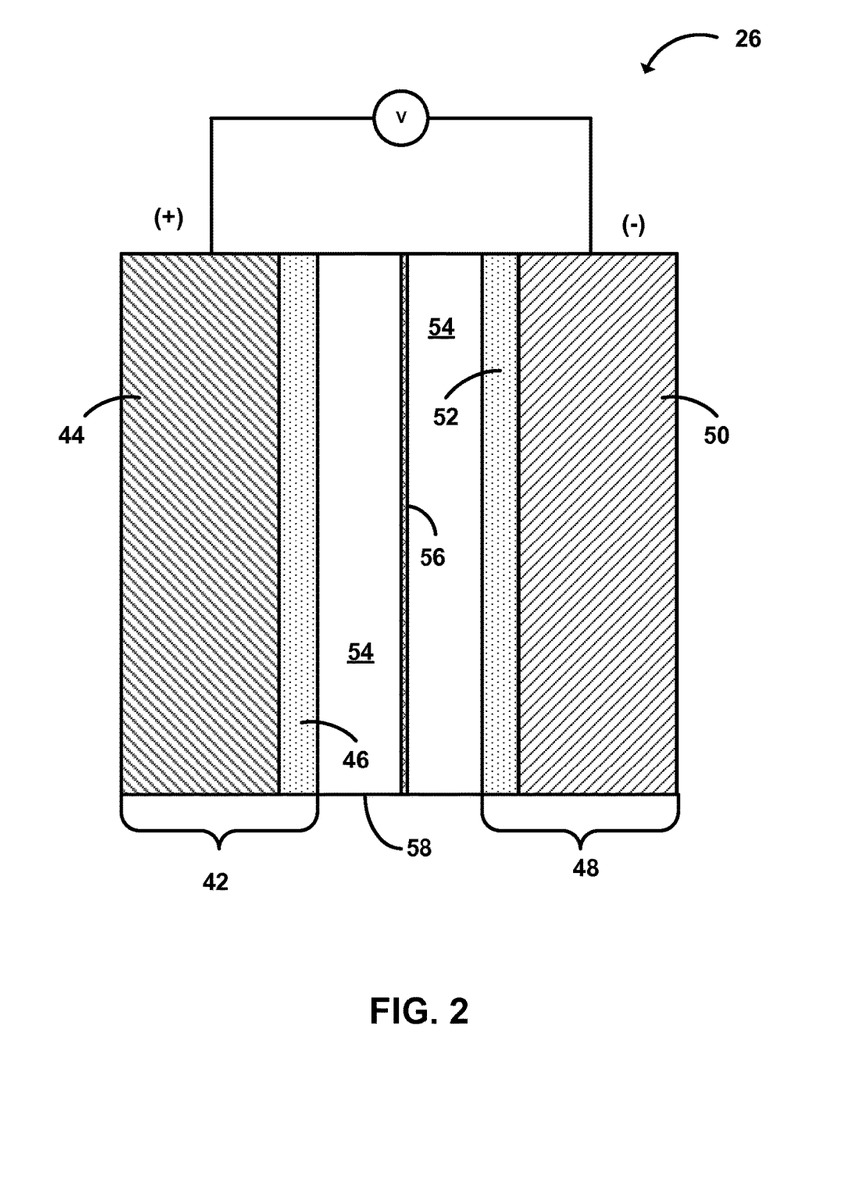
FIG. 2 is a cross-sectional diagram illustrating an example of a battery that may be used in an implantable medical device.

FIG. 2 is a cross-sectional diagram illustrating an example of battery 26 that may be used in an IMD 16. In particular, battery 26 may take the form of a lithium primary battery. As noted above, throughout the service life of battery 26, battery 26 may provide operational power for IMD 16 to deliver therapy to patient 12, e.g., in the form of electrical stimulation therapy, by converting chemical energy into electrical energy. As shown in FIG. 2, battery 26 includes first electrode 42, second electrode 48, and organic electrolyte 54. Depending on the configuration, battery 26 may also include separator 56 between first electrode 42 and second electrode 48. First electrode 42, second electrode 48, electrolyte 54, and separator 56 may all be enclosed within battery housing 58, which separates the internal components of battery 26 from the external environment, such as, e.g., the other internal components of IMD 16.

First electrode 42 may include a metal substrate 44 (e.g., a current collector) and a first electrode composition 46. Current collectors, as used herein, may refer to a material included in battery 26 to conduct electrons to or from the electrodes. In the example illustrated in FIG. 2, first electrode 42 may be a cathode (or positive electrode). In some examples, metal substrate 44 of first electrode 42 is a material that may be used as a current collector, such as a metal. In one example, metal substrate 44 may be formed from at least one of, but not limited to, aluminum, aluminum alloys, copper, copper alloys, titanium, titanium alloys, nickel, and nickel alloys.

First electrode 42 includes a layer of first electrode composition 46 on metal substrate 44. In FIG. 2, first electrode composition 46 may be a positive electrode composition. As illustrated in FIG. 2, the layer of first electrode composition 46 may be deposited on one major surface of metal substrate 44. However, first electrode composition 46 may be deposited on more than one surface of metal substrate 44, such as, e.g., on a first major surface and a second major surface of metal substrate 44.

In some examples, first electrode composition 46 may include at least one active material. As discussed herein, the electrode composition may be deposited onto metal substrate 44 via a solvent based solution. In FIG. 2, where the first electrode composition 46 is a positive electrode composition, the at least one active material may be selected from the group including, but not limited to, silver vanadium oxide, carbon monofluoride, lithium cobalt oxide, lithium nickel oxide, lithium manganese oxide, lithium iron phosphate. In one example, the active material includes at least silver vanadium oxide and carbon monofluoride ($CF_x$-SVO). Other active materials may include manganese dioxide ($MnO_2$), vanadium pentoxide ($V_2O_5$), and copper silver vanadium oxide ($Cu_xAg_{2-x}V_4O_{11}$).

In some examples, first electrode composition 46 may also include one or more additives, such as, e.g., a binder material, conductive additives, and combinations thereof. For example, the binder material include PTFE or PVDF or a sodium carboxymethylcellulose (Na-CMC) based binder and/or styrene-butadiene rubber. As discussed herein, depending on the battery type and battery application, the types and amounts of binder material may vary. The binder material may increase the adhesion between the active material and/or the conductive additives to the metal substrate 44. In some examples, the conductive additives of the first electrode composition 46 may include a carbonaceous materials. In one non-limiting example, the carbonaceous material may be carbon black. As discussed herein, depending on the battery type and battery application, the types and amounts of conductive additives may vary.

As described herein, the first electrode composition 46 (or cathode composition) may include at least one active material and a metal oxide or fluoride. The metal oxide or fluoride may be selected to exhibit a second discharge capacity at a voltage lower than the first discharge capacity of the active material of first electrode composition 46. As described herein, lithium from the anode composition 50 of second electrode 48 may react with the active material of first electrode composition 46 at the first discharge capacity during the operational life of battery 26 and, following the consumption of the active material of first electrode composition 46, the lithium of second electrode 48 may react with the metal oxide or fluoride of first electrode composition 46 at second discharge capacity less than that of the first discharge capacity of the active material. Such a reaction may take place prior to the lithium reacting with electrolyte 54 below a third discharge capacity. Example metal oxides and fluorides that may be incorporated into first electrode composition 46 may include cupric oxide (CuO), cuprous oxide ($Cu_2O$), and vanadium oxide ($V_2O_4$), chromium oxide ($Cr_2O_3$), vanadium fluoride ($VF_3$), Iron fluoride ($FeF_2$), bismuth fluoride ($BiF_3$) and manganese fluoride ($MnF_2$). By incorporating the metal oxide or fluoride into electrode composition of first electrode 42 may, for example, reduce or substantially eliminate the formation of gas within housing 58 of primary battery 26 that would normally result from the reaction of excess lithium with electrolyte 54.

Primary battery 26 also includes second electrode 48. Second electrode 48 may include a metal substrate 50 and a second electrode composition 52. In the example illustrated in FIG. 2, the second electrode 48 may be an anode (or negative electrode) and the second electrode composition 52 may constitute a negative electrode composition. Metal substrate 50 may be a current collector and may be selected from, but is not limited to, aluminum, aluminum alloys, copper, copper alloys, titanium, titanium alloys, nickel, and nickel alloys. Metal substrate 50 may include substantially the same or similar features as described in reference to metal substrate 44.

In the example where battery 26 is a lithium battery, the second electrode composition 52 may include a material or compound that includes lithium. Example lithium materials for second electrode composition 52 deposited on may include metallic lithium. As noted above, in some examples, second electrode composition 52 may include a metal source other than that of lithium as electron supply. Examples of such metals may include sodium, potassium, magnesium, and calcium. In some examples, the second electrode composition 52 may include other materials, such as other active materials and additives such as conductive additives and binders. As discussed herein, the type of battery and battery application may determine what types of materials are included in the second electrode composition 52.

As seen in FIG. 2, electrolyte 54 may separate positive electrode 42 from negative electrode 48. Electrolyte 54 may provide a medium through which ions (e.g., lithium ions) may travel. In one example, electrolyte 54 may be a liquid (e.g., a lithium salt dissolved in one or more non-aqueous solvents such as propylene carbonate and dimethoxyethane). In another example, the electrolyte 54 may be a lithium salt dissolved in a polymeric material such as poly(ethylene oxide) or silicone. In yet another example, the electrolyte may be an ionic liquid such as N-methyl-N-alkylpyrrolidinium bis(trifluoromethanesulfonyl)imide salts. In a further example, the electrolyte 54 may be a solid state electrolyte such as a lithium-ion conducting glass such as lithium phosphorous oxynitride (LiPON).

Various other electrolytes may be used according to other examples. For example, the electrolyte 54 may be a 1:1 mixture of propylene carbonate to dimethoxyethane in a 1.0 molar (M) salt of lithium hexafluoroarsenate (LiAsF$_6$), or 1:1 mixture of ethylene carbonate (EC) to diethylene carbonate (DEC) (EC:DEC) in a 1.0 molar (M) salt of lithium hexafluorophosphate (LiPF$_6$). Electrolyte 54 may include a polypropylene carbonate solvent and a lithium bis-oxalato-borate salt (sometimes referred to as LiBOB). The electrolyte 54 may comprise one or more of a polyvinylidene fluoride (PVDF) copolymer, a PVDF-polyimide material, and organosilicon polymer, a thermal polymerization gel, a radiation cured acrylate, a particulate with polymer gel, an inorganic gel polymer electrolyte, an inorganic gel-polymer electrolyte, a PVDF gel, polyethylene oxide (PEO), a glass ceramic electrolyte, phosphate glasses, lithium conducting glasses, lithium conducting ceramics, and an inorganic ionic liquid or gel, among others.

As also seen in FIG. 2, battery 26 may optionally include a separator 56. Separator 56 may be provided between the first electrode 42 and the second electrode 48. In one example, separator 56 may be a polymeric material such as a polypropylene/polyethelene or another polyolefin multi-layer laminate that includes micropores formed therein to allow electrolyte and lithium ions to flow from one side of the separator 56 to the other. Separator 56 may have a thickness within a range of from approximately 10 µm to 50 µm. In one example, the thickness of the separator is approximately 25 µm. Separator 56 may have an average pore size within the range of from approximately 0.02 µm to 0.10 µm.

A battery housing 58 may enclose first electrode 42, second electrode 48, electrolyte 54, and separator 56 of battery 26 of FIG. 2. Battery housing 58 may be made of stainless steel or suitable material. In one example, the battery case may be made of titanium, aluminum, or alloys thereof. The total volume enclosed by battery housing 58 may be influenced by a number of factors including, e.g., the size of electrodes 42 and 48, and volume of electrolyte. As noted above, the overall size of housing 58 may be influenced based on the amount of gas formed, if any, due to the reaction of any excess lithium of the second electrode 48 with electrolyte 54 following the consumption of the active material of first electrode 42, e.g., after the operational life of battery 26. For example, the volume of housing 58 must be selected such that the pressure within housing 58 does compromise the integrity of housing 58 due to the formation of gas following the consumption of the active material in the cathode, particularly in cases in which IMD 16 is not removed from patient 12 soon after the operational life of battery 26, if ever. As it is may be desirable to minimize the overall size of battery 26, it may be desirable in some cases to reduce or substantially eliminate the formation of gas from the reaction of any excess lithium in second electrode 48 with electrolyte 54 to reduce the overall size of battery housing 58. For example, in the case of electrolytes containing propylene carbonate (C$_4$H$_6$O$_3$), gas may be formed according to the following reaction:

$$2Li + C_4H_6O_3 \Rightarrow CH_3-CH=CH_2(\text{propylene gas}) + Li_2CO_3$$

As described herein, composition 46 of first electrode 42 may include one or more metal oxides or fluorides in addition to the active material and/or other additives. The metal oxide(s) or fluoride(s) may be such that, when the active material of first electrode composition 46 is substantially consumed by the reaction with the lithium of second electrode composition 52, the lithium reacts with the metal oxide or fluoride rather than electrolyte 54. The reaction of the metal oxide or fluoride may consume at least a portion of the excess lithium of second electrode 48 following the discharge of the active material of first electrode 42. In this manner, depending on the amount of metal oxide or fluoride in first electrode 42 compared to the excess lithium in second electrode 48, the amount of gas produced within the housing as a result of the reaction of the lithium with electrolyte 54 may be reduced or substantially eliminated within the battery housing. In some examples, the use of lithium primary battery 26 may allow for a decrease in overall size of housing 58 and IMD 16, and increase in packing density within battery 26 and IMD 16 compared to that of a medical device incorporating a lithium primary battery without such a metal oxide in the cathode composition.

Any suitable metal oxide or fluoride may be incorporated into first electrode composition 46 to react with the excess lithium of second electrode 48. In particular, one or more metal oxides and/or metal fluorides may be selected that exhibits a discharge capacity at a voltage that is lower than that of the active material in first electrode composition 46 but is greater than that of the discharge voltage of electrolyte 54 in the battery. Again, in such a case, lithium from the anode composition 50 of second electrode 48 may react with the active material of first electrode composition 46 at a first discharge capacity during the operational life of battery 26 and, following the consumption of the active material of first electrode composition 46, the lithium of second electrode 48 may react with the metal oxide or fluoride of first electrode composition 46 at second discharge capacity at a voltage lower than that of the first discharge capacity of the active material but greater than the third discharge capacity of electrolyte.

In some examples, the discharge capacity of the metal oxide and/or metal fluoride may be between about 2.6 Volts (V) and about 1.6 V, such as, between about 2.4 V and about 1.8 V. In some examples, such metal oxides and fluorides may include cupric oxide, cuprous oxide, and vanadium oxide, chromium oxide, vanadium fluoride, iron fluoride, bismuth fluoride and manganese fluoride. The discharge capacity of the active material may be greater than about 2.2 V, such as, between about 3.6 V and about 2.4 V, or greater than about 2.4 V. The discharge capacity of electrolyte 54 may be less than about 2 V, such as, e.g., less than 1.8 V. Materials with other discharge capacities are contemplated. The discharge capacity of a material may be determined using any suitable technique including, e.g., experimentation, modeling, scientific literature, and the like. At least a portion of range of discharge capacity of the metal oxide and/or metal fluoride may be less than that of the active material. In some examples, the discharge capacity range of the metal oxide and/or metal fluoride may overlap at a portion of that of the active material, while in other examples, the discharge capacity range may be entirely below that of the active material.

In some examples, the one or more metal oxides or fluorides of first electrode composition may have a true density (as opposed to a bulk density which may be influenced by particular size) that is approximately equal to or greater than that of the active material and/or additives of first electrode composition 46. The greater the density of the metal oxide or fluoride the lesser the overall volume of first electrode 42, which may reduce the overall volume of battery 26. In some examples, the metal oxide or fluoride may have a density of greater than approximately 3 grams per cubic centimeter, such as, e.g., greater than approximately 4 grams per cubic centimeter.

First electrode composition 46 may include any suitable amount of such a metal oxide and/or metal fluoride. For example, first electrode composition 46 may include an amount of metal oxide and/or fluoride selected such that at least a portion of any excess lithium of second electrode 48 reacts with the metal oxide and/or fluoride following the consumption of the active material to consume at least a portion of the excess lithium. In some examples, the metal oxide and/or fluoride may be provided in excess to consume substantially all excess lithium of second electrode 48 following the consumption of the active material by way of a lithium limited reaction. In some examples, the metal oxide and/or fluoride may be provided in excess to consume at least about 50%, such as, e.g., at least about 75% or at least about 85%, of the excess lithium of second electrode 48 following the consumption of the active material by way of a lithium limited reaction. In some examples, the amount of the metal oxide and/or fluoride in first electrode composition 46 may be limited by the impact on the volumetric capacity of the active materials. In some examples, the capacity ratio of excess lithium to metal oxide and/or fluoride may be between approximately 1.2 and approximately 0.5, such as, e.g., approximately 1. In some examples, first electrode composition 46 may include between approximately 40 percent and 5 percent metal oxide and/or metal fluoride, such as, e.g., between approximately 30 percent and 10 percent metal oxide and/or metal fluoride. Example metal oxides and metal fluorides may take the form of powders or be within a solution or emulsion, and may be incorporated with the active material using any suitable method. In some examples, the metal oxide and/or metal fluoride composition may be mixed or otherwise dispersed with the active material or may be present as a separate layer or portion in first electrode 42 from the active material.

Figure 3:
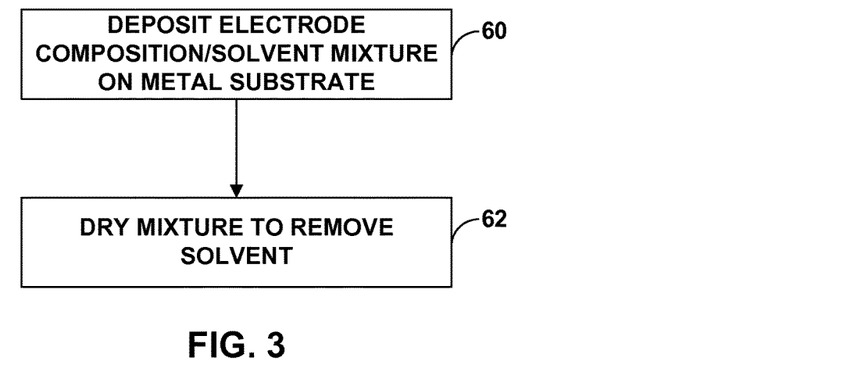
FIG. 3 is a flow diagram illustrating an example technique for forming an example electrode for use in a battery.

FIG. 3 is a flow diagram illustrating an example method of forming an example electrode structure, such as, e.g., electrode 42 of FIG. 2. For ease of illustration, the example of FIG. 3 is described with regard to electrode 42. As shown in FIG. 3, electrode composition 46 may be deposited onto at least one major surface of metal substrate 44 (60). In some examples, the first electrode composition 46, including the active material and metal oxide or fluoride, may be deposited onto the surface of substrate 44 in a solvent-based solution. In one example, the solvent may be selected from, but is not limited to, at least one of water and NMP depending, e.g., on what type of binder material is used. In some examples, the solvent is used in an amount approximately 50 wt. % of the first electrode composition 46.

In some example, the electrode composition may be deposited using a powder dispense/press process. For example, the electrode composition may be prepared in solvent(s), and the solvent(s) may be removed at elevated temperature. The resulting powder electrode composition may be pressed onto a metal substrate (current collector).

In some examples, the electrode composition may be deposited using a slurry coating process. For example, a slurry may be formed by mixing the electrode composition with a solvent. The electrode composition may be deposited onto the metal substrate using techniques known to those skilled in the art including, but not limited to, gravure coating, reverse roll coating, knife over roll coating, slot die coating, immersion coating, curtain coating, and air knife coating. As discussed herein, as the electrode composition is deposited onto the major surface of the metallic surface comprising the plurality of tunnels such that a portion of the electrode composition may be wicked into the plurality of tunnels via capillary action.

Following the deposition of electrode composition 46 onto metal substrate 44, composition 46 may be dried to remove all or a portion of the solvent from the mixture (62). For example, the deposited electrode composition may be heated to remove substantially all of the solvent. The electrode composition may be dried by using known techniques by those skilled in the art. Examples of drying the electrode composition may include, but are not limited to transfer of hot roll, a pass through a drying oven in the form of web as coated, simple placement in a drying oven as individual coupons, microwave energy, among others. The electrode composition may be dried at a temperature within a range of from approximately 50 degrees Celsius (° C.) to approximately 300° C.

In some examples, metal substrate 44 may also be compressed with electrode composition 46 to further attach electrode composition 46 on metal substrate 44. Metal substrate 44 and electrode composition 46 may be compressed using known techniques to those skilled in the art. Examples of techniques for compression include, but are not limited to direct pressing of coupons or calendared between rollers in the form of a passing web among others.

Figure 4:
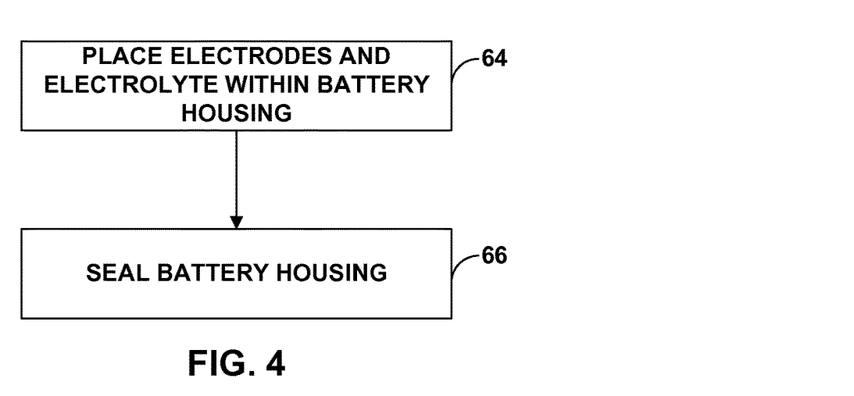
FIG. 4 is a flow diagram illustrating an example technique for assembling an example battery.

FIG. 4 is a flow diagram illustrating an example technique for assembling an example battery, such as, e.g., battery 26. For ease of illustration, the example of FIG. 3 is described with regard to battery 26. As shown in FIG. 4, first electrode 42 and second electrode 46 may be place within housing 58 of battery 26 along with electrolyte (64), e.g., via one or more openings in housing 58. Once within housing 58, any openings within housing 58 may be sealed to isolate the internal components of battery 26 from the outside environment (66).

Figure 5:
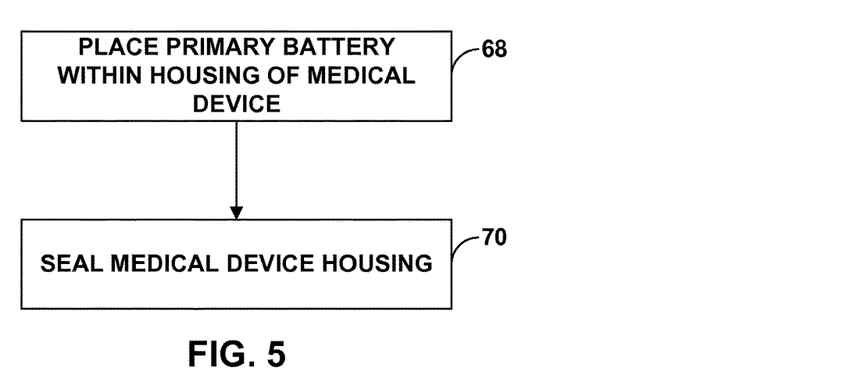
FIG. 5 is a flow diagram illustrating an example technique for assembling an example medical device including a battery.

FIG. 5 is a flow diagram illustrating an example technique for assembling an example medical device, such as, e.g., IMD 16 including battery 26. Once battery 26 is formed, e.g., via the technique of FIG. 3, battery 26 may be placed within outer housing 40 of IMD 16 via one or more opening in housing 40 along with the other internal components of IMD 16 (68). Outer housing 40 may then be hermetically sealed to isolate the internal components of IMD 16 from the outside environment (70).

Various examples have been described in the disclosure. These and other examples are within the scope of the following claims.

The invention claimed is:

1. A primary battery configured to supply operation power to an implantable medical device, the primary battery comprising:
a cathode comprising an active material and at least one of a metal oxide or a metal fluoride, wherein the active material exhibits a first discharge capacity and the at least one of the metal oxide or the metal fluoride exhibits a second discharge capacity at a voltage lower than the first discharge capacity;

a current collector, wherein the cathode comprises a cathode layer on the current collector, wherein the cathode layer is formed of a mixture of the active material and the at least one of the metal oxide or the metal fluoride;

an anode comprising a metal as an electron source; and an electrolyte between the cathode and anode, wherein the metal reacts with the electrolyte below a third discharge capacity at a voltage lower than the second discharge capacity to form a gas, wherein the metal reacts with the active material at the first discharge capacity to consume the active material, and, following the consumption of the active material of the cathode, the metal reacts with the at least one of the metal oxide or the metal fluoride of the cathode prior to reacting with the electrolyte below the third discharge capacity, and wherein the cathode includes an amount of the active material and the at least one of the metal oxide or the metal fluoride, and the anode includes an amount of metal such that an excess portion of the metal and an amount of the at least one of the metal oxide or the metal fluoride remains following the consumption of the active material, and wherein the amount of the at least one of the metal oxide or the metal fluoride is proportioned to consume all of the excess portion of the metal.

2. The battery of claim 1, wherein the second discharge capacity is between about 2.6 Volts and about 1.8 Volts.

3. The battery of claim 1, wherein the active material includes silver vanadium oxide (SVO) and carbon monofluoride (CFx).

4. The battery of claim 1, wherein the at least one of the metal oxide or the metal fluoride comprises at least one of cupric oxide, cuprous oxide, vanadium oxide, chromium oxide, vanadium fluoride, iron fluoride, bismuth fluoride and manganese fluoride.

5. The battery of claim 1, wherein the metal comprises lithium.

6. The battery of claim 1, wherein the at least one of the metal oxide or the metal fluoride has a true density of greater than approximately 3 grams per cubic centimeter.

7. The battery of claim 1, further comprising a separator between the anode and cathode.

8. The battery of claim 1, wherein the active material of the cathode includes a first active material and a second active material.

9. The primary battery of claim 1, wherein the cathode layer includes between approximately 30% by weight and 5% by weight of the at least one of the metal oxide or the metal fluoride.

10. The primary battery of claim 1, wherein the amount of the at least one of the metal oxide or the metal fluoride is such that all of the excess portion of the metal is consumed by the at least one of the metal oxide or the metal fluoride prior to reaction of the excess portion of the metal with the electrolyte.

11. The primary battery of claim 1, wherein the cathode comprises the active material and at least the metal fluoride.

12. The primary battery of claim 1, wherein the cathode comprises the active material, the metal fluoride, and the metal oxide.

13. An implantable medical device comprising:
a housing; and
a primary battery within the housing, wherein the implantable medical device is configured to operate on power supplied by the primary battery until an end of a service life of the battery, the primary battery comprising:

a cathode comprising an active material and at least one of a metal oxide or a metal fluoride, wherein the active material exhibits a first discharge capacity and the at least one of the metal oxide or the metal fluoride exhibits a second discharge capacity at a voltage lower than the first discharge capacity, an anode comprising a metal as an electron source, and an electrolyte between the cathode and anode, wherein the metal reacts with the electrolyte below a third discharge capacity at a voltage lower than the second discharge capacity to form a gas, wherein the metal reacts with the active material at the first discharge capacity during the service life of the battery to consume the active material, wherein the consumption of the active material at the first discharge capacity defines the end of service life of the battery, and, following the consumption of the active material of the cathode at the end of the service life of the battery, the metal reacts with the at least one of the metal oxide or the metal fluoride of the cathode prior to reacting with the electrolyte below the third discharge capacity, and wherein the cathode includes an amount of the active material and the at least one of the metal oxide or the metal fluoride, and the anode includes an amount of metal such that an excess portion of the metal and an amount of the at least one of the metal oxide or the metal fluoride remains following the consumption of the active material during the service life of the battery, and wherein the amount of the at least one of the metal oxide or the metal fluoride is proportioned to consume all of the excess portion of the metal.

14. The implantable medical device of claim 13, wherein the second discharge capacity is between about 2.6 Volts and about 1.8 Volts.

15. The implantable medical device of claim 13, wherein the active material includes silver vanadium oxide (SVO) and carbon monofluoride (CFx).

16. The implantable medical device of claim 13, wherein the at least one of the metal oxide or the metal fluoride comprises at least one of cupric oxide, cuprous oxide, vanadium oxide, chromium oxide, vanadium fluoride, iron fluoride, bismuth fluoride and manganese fluoride.

17. The implantable medical device of claim 13, wherein the cathode includes between approximately 30% by weight and 5% by weight of the at least one of the metal oxide or the metal fluoride.

18. The implantable medical device of claim 13, wherein the metal comprises lithium.

19. The implantable medical device of claim 13, wherein the at least one of the metal oxide or the metal fluoride has a true density of greater than approximately 3 grams per cubic centimeter.

20. The implantable medical device of claim 13, wherein the battery further comprises a separator between the anode and cathode.

21. The implantable medical device of claim 13, further comprising a current collector, wherein the cathode comprises a cathode layer on the current collector, wherein the cathode layer is formed of a mixture of the active material and the at least one of the metal oxide or the metal fluoride.

22. The implantable medical device of claim 21, wherein the active material of the cathode includes a first active material and a second active material.

23. The implantable medical device of claim 21, wherein the amount of the at least one of the metal oxide or the metal fluoride is such that all of the excess portion of the metal is consumed by the at least one of metal oxide and metal fluoride prior to reaction of the excess portion of the metal with the electrolyte.

24. The implantable medical device of claim 13, wherein the implantable medical device is configured to not operate on power from the primary battery after the end of the service life of the battery while the excess portion of the metal is consumed by the at least one of the metal oxide or the metal fluoride prior to reaction of the excess portion of the metal with the electrolyte.

25. The implantable medical device of claim 13, further comprising:
   an electrical signal generator configured to generate electrical stimulation;
   a sensing module configured monitor electrical activity of a heart of a patient; and
   a processor configured to control the electrical signal generator to delivery electrical stimulation to the patient via one or more electrodes, wherein the implantable medical device is configured such that the primary battery supplies power to operate the electrical signal generator, the sensing module, and the processor until the end of the service life of the battery.

26. The implantable medical device of claim 13, wherein the cathode comprises the active material and at least the metal fluoride.

27. The implantable medical device of claim 13, wherein the cathode comprises the active material, the metal fluoride, and the metal oxide.

* * * * *